United States Patent [19]

Schabron

[11] Patent Number: 4,576,917

[45] Date of Patent: Mar. 18, 1986

[54] METHOD FOR ANALYSIS OF ADDITIVES IN POLYOLEFINS

[75] Inventor: John F. Schabron, Bartlesville, Okla.

[73] Assignee: Phillips Petroleum Company, Bartlesville, Okla.

[21] Appl. No.: 187,873

[22] Filed: Sep. 17, 1980

[51] Int. Cl.[4] ...................... G01N 30/14; G01N 33/44

[52] U.S. Cl. ........................................ 436/85; 422/70; 422/101; 436/111; 436/128; 436/161; 436/177

[58] Field of Search ..................... 23/230 M, 230 HC; 436/85, 111, 128, 161, 177

[56] References Cited

U.S. PATENT DOCUMENTS 4,059,020 11/1977 Avakian .......................... 422/101 X

FOREIGN PATENT DOCUMENTS 926617 5/1963 United Kingdom ............ 23/230 M

OTHER PUBLICATIONS

Analysis of Stabilizers and Antioxidants in Plastics; M. J. Telepchak, Apr. 1974, Perkin-Elmer Liq. Chrom. Applic. Study 37.

Swarin et al., J. of Applied Polymer Sci., vol. 19, pp. 1243-1256 (1975).

Lichtenthaler et al., J. Chromatogr., 1978, 149, 533.

Scott et al., Eur. Poly. J., vol. 16, pp. 497-501, 1980.

*Primary Examiner*—Arnold Turk

*Attorney, Agent, or Firm*—Edward L. Bowman

[57] ABSTRACT

A process is provided for the analysis of additives in polyolefins involving dissolving the polyolefin in decalin and subsequently precipitating the polymer, isolating a portion of the extract and measuring the additives therein. Apparatus for use in the process are also disclosed.

12 Claims, 4 Drawing Figures

31

18

32

METHOD FOR ANALYSIS OF ADDITIVES IN POLYOLEFINS

This invention relates to the analysis of additives in polyolefins.

Most polyolefin compositions employ antioxidants, heat and light stabilizers and antiozonauts, either alone or in combination to protect the polymer from degradation due to heat and oxidation. To insure that additives or combinations of additives have been added properly to polyolefin batches following synthesis of the polymer, there is a need for reliable and rapid methods for analyzing the quantities of those additives.

Since the additives are generally present in low concentrations, e.g., 0.01 to 1 weight percent, and since the additives generally have closely related chemical functionality, analysis generally requires the extraction of the additives from the polymer followed by chromatographic separation and detection of the individual additives. Obviously, for the best results there is a need for a method of extraction which consistently results in a substantially quantitative removal of the additives from the polyolefin. Also, it is desirable for the separation to be such that the additives are removed relatively quickly from the polymer. However, the speed of the separation is limited somewhat by the fact that conditions must be selected which do not cause significant decomposition or reaction of the additives.

A number of the prior art techniques of separating the additives from the polymer are disclosed by A. M. Wims and S. J. Swarin in *Journal of Applied Polymer Science,* 19, pp. 1243–1256 (1975). These techniques all involved either lengthy treatments of ground polyolefin or heating under relatively high temperature conditions. The British Standard Method involves dissolving ground polyethylene in refluxing toluene for at least an hour followed by precipitation of the polymer by the addition of either ethanol or methanol. This method requires constant operator attention and the rigorous conditions can lead to some additive decomposition. Another method involves the shaking of 50 mesh polyolefin with chloroform for 72 hours at room temperature. Another room temperature extraction involved shaking 8 mesh polyolefin in tetrahydrofuran for 24 hours. When methylene chloride substituted for the tetrahydrofuran in the room temperature extraction only 50 percent of the additives were separated from the polyolefin in the 24 hour period.

An object of the present invention is to provide an analysis method in which additives can be more quickly removed from polyolefins under temperature conditions that do not have an adverse effect upon the reliability of the analysis.

Another object of the present invention is to provide a method for the analysis of additives in polyolefins which is amenable for use in an automated analysis system.

Still another object of the present invention is to provide an analysis system suitable for repetitive analysis of the additives in polyolefins.

Yet another object of the present invention is to provide an apparatus for enabling the removal of a sample of a polyolefin extract substantially free of polyolefin.

Other objects, aspects, and advantages of the present invention will be apparent from the following description and the appended drawings.

SUMMARY OF THE INVENTION

In accordance with the present invention, there is provided a process for the analysis of additives in polyolefins comprising (a) dissolving the polyolefin in hot decalin; (b) cooling the polyolefin-decalin solution to precipitate the polyolefin; (c) recovering from the resulting decalin solution a portion that is substantially free of polyolefin; (c) separating said portion into various chemical components; and (e) determining the relative amounts of the components by means of a detector.

In accordance with another aspect of the present invention, there is provided an analysis system suitable for repetitive analysis of the additives in polyolefins comprising (a) a vessel in which said polyolefin can be dissolved in a heated solvent; (b) a heating means capable of heating a mixture of solvent and polyolefin in said vessel to effect dissolution of the polyolefin; (c) stirring means for stirring the solvent while said polyolefin is being dissolved; (d) a cooling means capable of cooling the polyolefin solution to precipitate the polyolefin; (e) a sample withdrawal means including a filter capable of substantially precluding introduction of polyolefin in the sample that is withdrawn; (f) a liquid chromatography column for separating various components of the sample; (g) means for conveying a selected quantity of said sample to said column; (h) a detector means for detecting the relative amounts of said components; and (i) a recording means capable of recording the relative amounts of said components as detected by said detector means.

In accordance with still another aspect of the present invention, there is provided an apparatus enabling the removal of a sample of a polyolefin extract substantially free from polyolefin comprising a sample withdrawal means having a filter means capable of substantially precluding the introduction of polyolefin in the sample that is withdrawn.

DETAILED DESCRIPTION OF THE INVENTION

The method of the present invention is generally applicable to any of the polyolefins that are substantially insoluble in decalin at temperatures in the range of about 15° C. to about 27° C. The method is particularly well suited for the analysis of the additives in polyolefins consisting essentially of polyethylene.

Although the polyolefin can be ground into small particles, the method can be employed on generally any type of polyolefin composition. The method is especially well suited for use in dissolving conventional pellets generally having dimensions in the range of about 0.01 mm to 10 mm.

The temperature required to dissolve the polyolefin can vary somewhat depending upon the particular polyolefin and the speed with which dissolution is desired. Generally, it is preferred that the polyolefin be mixed with decalin at a temperature of about 90° C. to about 120° C., most preferably about 110° C.

Generally, the cooling can begin as soon as the polyolefin has been completely dissolved. However, routine experimentation can reveal whether additional time is necessary for obtaining quantitative removal of the additives of interest.

The cooling can be achieved in any manner that results in precipitation of substantially all of the polyolefin. Generally, this involves cooling the decalin to a temperature in the range of about 15° C. to about 27° C.

In order to obtain more rapid cooling, it is preferable to contact the vessel containing the decalin with a cooling medium having a temperature lower than the temperature to which the solution is to be cooled. Generally, it is desirable to settle on a standard set of heating and cooling conditions since vaporization of the decalin can affect the results of the analysis. Using substantially similar conditions in an analysis routine will thus minimize the chance of errors in evaluating the additive level of different lots of polymer.

The optimum amount of decalin for use with the polyolefin can be determined by routine experimentation and is of course somewhat dependent upon the level of the additives and the detection limits of the detector. Typically, one can use about 1 to about 8 grams of polymer per 100 milliliters of decalin. Preferably, about 4 grams of polymer is employed per 100 milliliters of decalin.

The present invention is applicable to many of the additives generally used in polyolefins. Routine experimentation can reveal whether suitable results can be obtained for a given additive. The technique is particularly well suited for the analysis of hindered phenol antioxidants that are generally used in such compositions. Typical examples of additives to which the present invention is generally applicable include 2,6-di-tert-butyl-4-methylphenol; octadecyl-3,5-ditert-butyl-4-hydroxyhydrocinnamate; tetrakis(methylene(3,5-ditertbutyl-4-hydroxyhydrocinnamate)methane; 4,4'-thiobis(6-tert-butyl-mcresol); 2-hydroxy-4-n-octoxy-benzophenone; 1,3,5-trimethyl-2,4,6-tris(3,5-di-tert-butyl-4-hydroxybenzyl)benzene; tris(3,5-di-tertbutylhydroxybenzyl)iso-cyanurate; 1,13-tris(2-methyl-4-hydroxy-5-tertbutylphenyl)butane.

If a particular additive of interest is not extracted in a suitably quantitative manner, it may be desirable to use in addition to the decalin a second solvent, or cosolvent, having greater solubility for that specific additive.

In order to minimize the possibility of oxidation of the additives, it may be desirable under some circumstances to carry out the extraction process under an inert gas such as nitrogen.

After the polymer has been dissolved and then precipitated, a sample portion of the decalin solution is withdrawn for separation into various chemical components. Any suitable sampling means can be employed. Preferably, the sampling means will be equipped with a filter capable of insuring that the sample withdrawn will be substantially free of polyolefin. Typically filters of 30 micron size or smaller are suitable.

The type of separation technique useful for particular type additives can be determined by routine experimentation. Several types of high performance liquid chromatography have been used for the separation of polymer additives. Examples include size exclusion, reverse phase, and normal phase. A separation technique which has been found to be particularly useful involves the use of a normal phase system using a porous microparticulate silica gel stationary phase, i.e., μ-Porasil (Waters Associates), with a heptane to methylene chloride 5 minute linear mobile phase gradient at 2 mL/minute. The normal phase chromatographic system could be used for the separation of various additive packages by changing the time and type of gradient (concave, convex, or linear) or by modifying the mobile phase and/or stationary phase.

Any suitable detector means can be employed, i.e., ultraviolet, fluoresence, conductivity, infrared, and refractive index detectors. An ultraviolet detector set at 280 nm is particularly well suited for the analysis of hindered phenol type additives.

In the drawings provided herewith, FIG. 1 is a partially cut away perspective view of a sampling device particularly suitable for use in the present inventive method.

Figure 1:
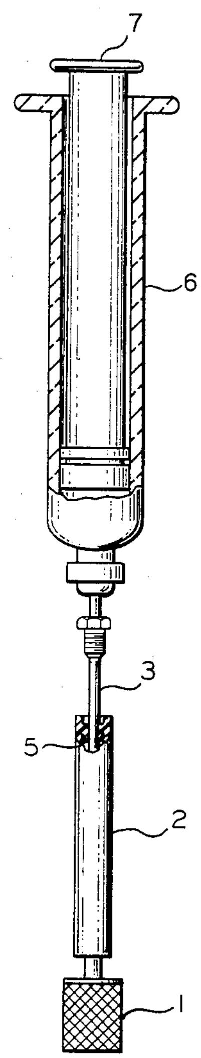

The apparatus illustrated in FIG. 1 will be explained in more detail below. The apparatus in FIG. 2 comprises mixing vessels 10, a loading table 11, a heating station 12, a cooling station 13, and a holding pan 14. The apparatus further includes a sample withdrawal means 15. The sample withdrawal means is connected in turn to an air actuated six port sampling valve 16 which is connected to a liquid chromatograph 17 and an injection control means 18 which is connected to a vacuum source 19.

The heating station 12 comprises a heating plate having an activator for turning the magnetic stirring bars that are placed in the decalin along with the polyolefin. The cooling station similarly comprises a cooling plate and an activator for turning the magnetic stirring bars.

The sample withdrawal means 15 is connected through tubing to the vacuum source 19. It is further adapted to being lowered into a vessel 10 and for being raised, rotated, and then lowered into a wash vessel 27 containing decalin. The sample withdrawal means comprises a hollow tube 28 having a filter 29 connected to its open end. The filter 29 has a generally non-porous extension 30 having dimensions at least as great as those of the filter means.

Figure 3:
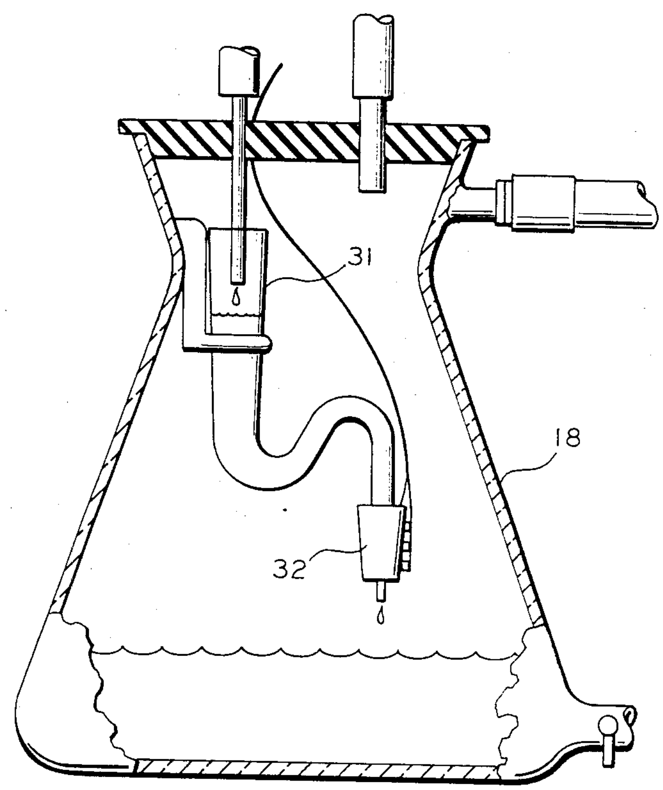
FIG. 3 is a cross-sectional enlarged view of the injection control means 18 of the apparatus of FIG. 2.

The injection control means 18 is further illustrated in FIG. 3 and comprises a vacuum flask equipped with a Waters liquid volume indicator 31 and siphon cell 32. The volume indicator 31 is connected to a programmer 33, the function of which will be made more clear shortly. The vacuum line is provided with a solenoid valve 34 for controlling vacuum. A similar valve 35 is provided to vent the flask.

Figure 4:
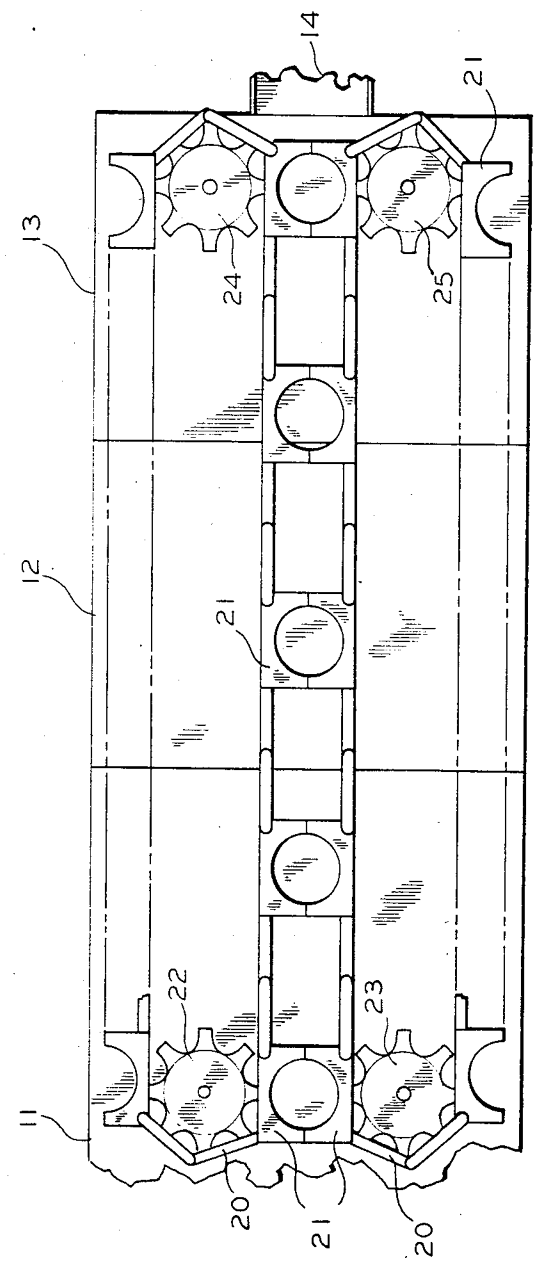
FIG. 4 is a top view of a vessel conveying apparatus suitable for automating apparatus of the type illustrated in FIG. 2.

The apparatus of FIG. 4 comprises two pair of chain loops 20 each having a plurality of spaced apart vessel holding means 21 preferably made of a material which quickly dissipates heat. The chain loops are mounted on sprockets 22, 23, 24, and 25. Sprocket 22 is a motor driven gear sprocket adapted to cause chain 20 to rotate around sprockets 22 and 23 and thus advance any vessel placed between two opposing vessel holding means 21.

Figure 2:
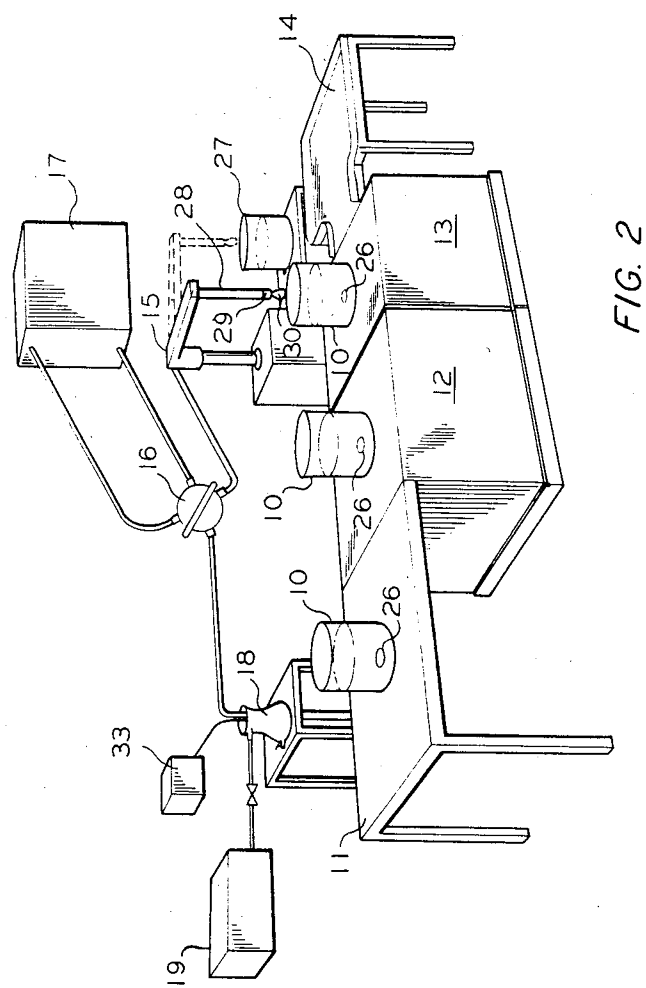
FIG. 2 is a perspective diagramatic view of apparatus suitable for polyolefin analysis using the present inventive technique.

In operation of a device of the type illustrated in FIGS. 2 and 3, a known specific quantity of polyolefin and a known volume of decalin are added to a mixing vessel placed on the loading table between two oppositely deposed adjacent holding means 21. Also a magnetic stirring bar 26 is added to the decalin. The motor driven sprocket is activated in response to programmer 33 and moves the vessel from the loading table 11 to the heating station 12.

When the beaker is positioned on the heating station, a microswitch, not shown, will be triggered and halt the movement of the sprocket 22. Thus, the vessel 10 will be maintained on the heating station for a predetermined time suitable for dissolving the polyolefin.

After the passage of the specified time, the sprocket 22 is reactivated by the programmer to move the vessel from the heating station 12 to the cooling station. After a specified period of time sufficient to precipitate the polyolefin, the sample withdrawal means is raised from the decalin wash 27, pivoted and lowered into the vessel resting at the cooling station. The spherical extension 30 pushes aside any polyethylene precipitate that it encounters to clear a path around the filter 29. This lowering of the sample withdrawal means activates another microswitch, not shown, which causes the programmer to allow a vacuum from vacuum source 19 to be drawn on the injection control means. Sample is drawn through the sample loop of the sampling valve 16 and into the siphon cell of the injection control means 18. After a predetermined amount of liquid has been sensed by the liquid volume indicator 31, thus insuring that the sample loop of the sampling valve is full, a signal is sent out which causes the vacuum to be discontinued and shortly thereafter the sampling valve is switched to the inject position which allows the sample in the sample loop of the sampling valve 16 to be carried to the chromatograph. The programmer simultaneously sends a signal which initiates the solvent program of the chromatograph and activates a recorder on the chromatograph to indicate that a run has begun.

The sample withdrawal means is then removed from the sample solution and placed in the decalin wash. The programmer then switches the sample valve back to the load position, the vacuum is again drawn on the vacuum flask and decalin is drawn through the sample loop of the sample valve. After the volume indicator senses that a sufficient volume of decalin has been drawn through the loop to clean the loop, the programmer discontinues the vacuum and the system is ready for the next sample to be placed upon the cooling station.

It is to be noted that the preceding description of the automated system is just provided for illustrating the invention. Many modifications within the scope of this invention will be readily obvious to those skilled in the art. For example, the vessel conveying means could readily be a turret means or any other suitable means rather than a chain drive means.

A further understanding of the inventive method and its advantages will be provided in the following examples.

EXAMPLE I

Polyethylene containing Naugard BHT, i.e., 2,6-di-tert-butyl-4-methyphenol; Irganox 1076, i.e., octadecyl-3,5-di-tert-butyl-4-hydroxyhydrocinnamate, and Irganox 1010, i.e., tetrakis(methylene (3,5-di-tertbutyl-4-hydroxyhydrocinnamate))methane, was analyzed in accordance with the present invention.

In each analysis about 2 grams of the polyethylene in the form of pellets was combined with 50 milliters of decalin. The mixture was heated to 110° C. on a hot plate with gentle stirring until dissolution was complete, generally about 30 minutes. To precipitate the polyethylene, the solutions were placed in an ice bath and cooled rapidly to room temperature with gentle stirring.

A sample for analysis was removed using a sample filtering apparatus of the type illustrated in FIG. 1 comprising a Waters 20–30 micron stainless steel solvent reservoir filter 1 connected to one end of about 5 inches of 3 mm inside diameter Teflon tubing 2. The other end of the tubing was connected to a 11/2 inch long blunt 16 gauge Luer lock needle 3 with a 1/16 inch stainless steel nut 4 and ferrule 5 at the end of the needle. The needle was connected to a Hamilton No. 1010W gastight 10 mL syringe 6 with Teflon plunger 7.

The precipitated polyethylene was pushed aside with a microspatula and the porous filter inserted into the solution and about 5 to 10 mL of the solution was drawn into the syringe. The filtered solution was then dispensed into a small vial and analyzed using a Waters Model 204 liquid chromatograph equipped with two Model 6000-A pumps, a Model 660 solvent programmer, and a U6K injector. Elution was monitored with a Waters Model 450 variable wavelength detector set at 280 mm and a 10 mV strip chart recorder.

The column used was a 3.9 mm inside diameter ×30 cm μ-Porasil column packed with 10 micron porous silica obtained from Waters Associates, Milford, MA.

The Model 660 programmer was set linear from 100 percent heptane to 100 percent methylene chloride for a 5 minute interval with a flow rate of 2 mL/minute.

The amount of each additive was determined from each sample injection by comparing peak heights for samples and standards. A blank decalin injection was made to determine the base line from which the peak heights should be measured.

The results for six replicate runs showed good precision for the method. The relative standard deviations were 1.2 percent for BHT, 1.3 percent for Irganox 1076 and 2.0 percent for Irganox 1010.

EXAMPLE II

In order to evaluate the effect of the amount of polyethylene dissolved in a given quantity of decalin, duplicate analysis were made using about 1 g, 2 g, and 4 g of polyethylene containing the three additives mentioned in Example I. The results are shown in Table I.

TABLE I

| Sample Amount, g | Amount Found, Wt. % | | |
|---|---|---|---|
| | BHT | Irganox 1076 | Irganox 1010 |
| 1.03 | 0.046 | 0.045 | 0.034 |
| 0.99 | 0.046 | 0.047 | 0.034 |
| 3.96 | 0.048 | 0.053 | 0.040 |
| 4.05 | 0.049 | 0.056 | 0.041 |
| 2.07 | 0.047 | 0.053 | 0.040 |
| 1.91 | 0.049 | 0.053 | 0.040 |

The results show the absence of significant error. The amounts of additives found for sample amounts of about 1 g vary slightly from sample amounts of 2 g and 4 g. This is probably due to measurement of smaller HPLC peaks at low sample amounts and further indicates the advantage of selecting a standard procedure for use in routine analysis of production lots of polymer.

EXAMPLE III

Spiking experiments were performed by dissolving additive-free polyethylene samples in decalin containing known amounts of BHT, Irganox 1076 and Irganox 1010. Duplicate runs were made using about 0.02 percent, 0.05 percent, and 0.1 percent of each additive, respectively. The results are summarized in Table II.

TABLE II

| Amount Added, mg | | | Amount Found, mg | | | Percent Recovered | | |
|---|---|---|---|---|---|---|---|---|
| BHT | 1076 | 1010 | BHT | 1076 | 1010 | BHT | 1076 | 1010 |
| 0.51 | 0.50 | 0.51 | 0.53 | 0.51 | 0.44 | 104 | 101 | 88 |
| 0.51 | 0.50 | 0.51 | 0.53 | 0.52 | 0.46 | 104 | 105 | 92 |
| 1.02 | 1.00 | 1.01 | 1.09 | 1.10 | 1.05 | 107 | 109 | 104 |
| 1.02 | 1.00 | 1.01 | 1.08 | 1.07 | 1.02 | 106 | 107 | 101 |
| 2.04 | 2.01 | 2.02 | 2.06 | 2.09 | 2.01 | 101 | 104 | 99 |
| 2.04 | 2.01 | 2.02 | 2.14 | 2.16 | 2.08 | 105 | 108 | 103 |

The results show good recoveries of all three additives.

Spiking experiments were also performed for three different polyethylene samples containing at least one or two additives. Prior to the spiking experiments duplicate analyses of each sample were carried out in the manner set forth in Example I. The analyses revealed that Sample A contained about 0.039 weight percent of Irganox 1010, Sample B about 0.021 weight percent of BHT and about 0.11 weight percent Irganox 1010, and Sample C about 0.011 weight percent BHT. The results of duplicate spiking experiments on those samples are listed in Table III wherein the quantities set forth under "Amount added" refer to the amount of the specified additive added to the decalin and wherein the quantities set forth under "Amount Found" refer to the amount of the specified additive found minus the amount that was present initially in the polyethylene.

TABLE III

| | | Amount Added, mg | | | Amount Found, mg | | | Percent Recovered | | |
|---|---|---|---|---|---|---|---|---|---|---|
| Sample | Amount, g | BHT | Irganox 1076 | Irganox 1010 | BHT | Irganox 1076 | Irganox 1010 | BHT | Irganox 1076 | Irganox 1010 |
| A | 1.96 | 1.02 | 1.00 | 1.01 | 1.04 | 1.08 | 1.03 | 103 | 108 | 102 |
| A | 2.01 | 1.02 | 1.00 | 1.01 | 1.06 | 1.10 | 1.13 | 104 | 110 | 112 |
| B | 2.02 | 1.02 | 1.00 | 1.01 | 1.02 | 1.07 | 0.99 | 100 | 107 | 98 |
| B | 1.97 | 1.02 | 1.00 | 1.01 | 0.99 | 1.09 | 0.94 | 98 | 109 | 93 |
| C | 1.97 | 1.02 | 1.00 | 1.01 | 1.04 | 1.05 | 0.98 | 102 | 105 | 97 |
| C | 2.04 | 1.02 | 1.00 | 1.01 | 1.07 | 1.06 | 1.05 | 105 | 106 | 104 |

Recoveries for the additives for most of the spiking experiments generally tended to be near or slightly above 100%. The recoveries of more than 100% were probably due to some evaporative loss of decalin and will not seriously affect the reliability of the method so long as substantially similar conditions are maintained in the analysis routine.

The preceding examples have been provided only for the purpose of illustrating specific embodiments of the present invention. Modifications and variations can be made which are clearly within the scope of the present invention.

What is claimed is:

1. A process for the analysis of hindered phenol antioxidants in polyolefins consisting essentially of:

(a) dissolving the polyolefin in hot decalin;

(b) cooling the polyolefin decalin solution by indirect heat exchange to precipitate the polyolefin;

(c) recovering from the resulting decalin solution a portion that is substantially free of polyolefin;

(d) separating said portion into various chemical components; and (e) determining the relative amounts of the components by means of a detector.

2. A process according to claim 1 wherein said polyolefin is dissolved in said decalin by stirring at a temperature in the range of about 90° C. to about 120° C.

3. A process according to claim 2 wherein said polyolefin is polypropylene.

4. A process according to claim 2 wherein said polyolefin is polyethylene.

5. A process according to claim 2 wherein said polyethylene contains at least one of 2,6-di-tert-butyl-4-methylphenol, octadecyl-3,5-di-tert-butyl-4-hydroxyhydrocinnamate, and tetrakis(methylene(3,5-di-tert-butyl-4-hydroxyhydrocinnamate)methane.

6. A process according to claim 2 wherein the additives in said polyethylene consist essentially of at least one of 2,6-di-tert-butyl-4-methylphenol, octadecyl-3,5-di-tert-butyl-4-hydroxyhydrocinnamate, and tetrakis(-methylene(3,5-di-tert-butyl-4-hydroxyhydrocinnamate))methane.

7. A process according to claim 2 wherein the recovered portion of the decalin solution is separated into various chemical components by liquid chromatography.

8. A process according to claim 7 wherein the stationary phase in the chromatography is a silica support.

9. A process according to claim 8 wherein said chromatography is normal phase chromatography and the mobile phase is a heptane to methylene chloride gradient.

10. A process according to claim 9 wherein said polymer is polyethylene.

11. A process according to claim 10 wherein said polyethylene contains at least one of 2,6-di-tert-butyl-4-methylphenol, octadecyl-3,5-di-tert-butyl-4-hydroxyhydrocinnamate, ad tetrakis(methylene(3,5-ditert-butyl-4-hydroxyhydrocinnamate))methane.

12. A process according to claim 11 wherein the additives in said polyethylene consist essentially of at least one of 2,6-di-tert-butyl-4-methylphenol, octadecyl-3,5-di-tert-butyl-4-hydroxyhydrocinnamate, and tetrakis(methylene(3,5-di-tert-butyl-4-hydroxyhydrocinnamate))methane.

* * * * *

UNITED STATES PATENT AND TRADEMARK OFFICE

CERTIFICATE OF CORRECTION

PATENT NO. : 4,576,917

DATED : March 18, 1986

INVENTOR(S) : John F. Schabron

It is certified that error appears in the above-identified patent and that said Letters Patent is hereby corrected as shown below:

Please add to the first page of the patent the following:

-- Inventor: Lyle E. Fenska --

Signed and Sealed this

Fourteenth Day of October, 1986

[SEAL]

*Attest:*

DONALD J. QUIGG

*Attesting Officer* *Commissioner of Patents and Trademarks*